US00PP19555P3

(12) United States Plant Patent
Folsom

(10) Patent No.: US PP19,555 P3
(45) Date of Patent: Dec. 9, 2008

(54) ALMOND TREE NAMED 'FOLSOM'

(50) Latin Name: *Prunus dulcis*
Varietal Denomination: Folsom

(75) Inventor: Albert Edwin Folsom, Clovis, CA (US)

(73) Assignee: Albert E. Folsom, Fresno, CA (US); Separate Property Living Trust ( * ) Notice: Subject to any disclaimer, the term of this patent is extended or adjusted under 35 U.S.C. 154(b) by 298 days.

(21) Appl. No.: 10/918,859

(22) Filed: Aug. 16, 2004

(65) Prior Publication Data

US 2006/0037115 P1 Feb. 16, 2006

(51) Int. Cl.
*A01H 5/00* (2006.01)

(52) U.S. Cl. ..... Plt./155

(58) Field of Classification Search ..... Plt./155
See application file for complete search history.

(56) References Cited

U.S. PATENT DOCUMENTS

PP15,049 P2 * 7/2004 Kochi ..... Plt./155
2006/0037115 P1 * 2/2006 Folsom ..... Plt./155

* cited by examiner

*Primary Examiner*—Wendy C. Haas
(74) *Attorney, Agent, or Firm*—Stratton Ballew PLLC

(57) ABSTRACT

An almond tree (*Prunus dulcis*) named 'Folsom' that blooms and ripens in the early season and produces a high quality, marketable crop.

5 Drawing Sheets

Latin name of the genus and species of the plant claimed: *Prunus dulcis*.
Variety denomination: 'Folsom'.

BACKGROUND OF THE INVENTION

The present invention relates to a new and distinct variety of almond tree that has been given the name 'Folsom'.

The original plant was discovered in the early 1960's as a mature tree growing in an orchard of 'Nonpareil' (non-patented) and 'Thompson' (U.S. Plant Pat. No. 1,526) almond trees located on the N.W. corner of Millbrook and Alluvial Avenues in Fresno, Calif. The inventor noted that the 'Nonpareil' trees developed symptoms of "non-infectious bud failure" while a particular tree, the 'Folsom' tree, remained productive and did not exhibit symptoms of the disorder. It was further noted that the 'Folsom' tree bloomed and harvested at the same time as the 'Nonpareil' and exhibited similar nut quality and characteristics.

'Nonpareil' is one of the most desirable cultivars grown because of its excellent quality and earliness of harvest. The 'Nonpareil' also requires cross-pollination because it is not self-fertile. A variety that exhibits similar characteristics in bloom, nut quality, and harvest and can pollinate the 'Nonpareil' would be desirable to plant. The 'Folsom' almond has exhibited these characteristics and under controlled conditions has been shown to pollinate 'Nonpareil'.

ASEXUAL REPRODUCTION

The first asexual reproduction of the new variety occurred in the late 1980s when wood was collected from the original tree and grafted onto an existing tree in the inventor's orchard located at 8520 N. Chestnut Ave., Clovis, Calif. Three additional trees were grafted on the inventor's property in the late 1990s.

Budwood from these trees was collected in 2001, and budded onto one each of 'Nemaguard' (non-patented) and 'Atlas' (U.S. Plant Pat. No. 8,913) rootstock at 21200 E. Dinuba Ave., Reedley, Calif.

All asexually reproduced trees exhibit similar characteristics as described herein and are similar to those characteristics observed by the inventor on the original 'Folsom' tree.

BRIEF SUMMARY OF THE INVENTION

The 'Folsom' almond tree is characterized principally to novelty by producing a consistently high quality nut similar to the 'Nonpareil' variety. The present cultivar blooms with and is harvested at the same time as the 'Nonpareil'.

Further, tree vigor, growth habit, and productivity appear to be similar to 'Nonpareil'. Under controlled conditions, 'Folsom' has been shown to pollinate the self-infertile variety 'Nonpareil', which is a desirable characteristic, and which needs to be further investigated in field trials.

DETAILED DESCRIPTION OF VARIETY

Figure 1:
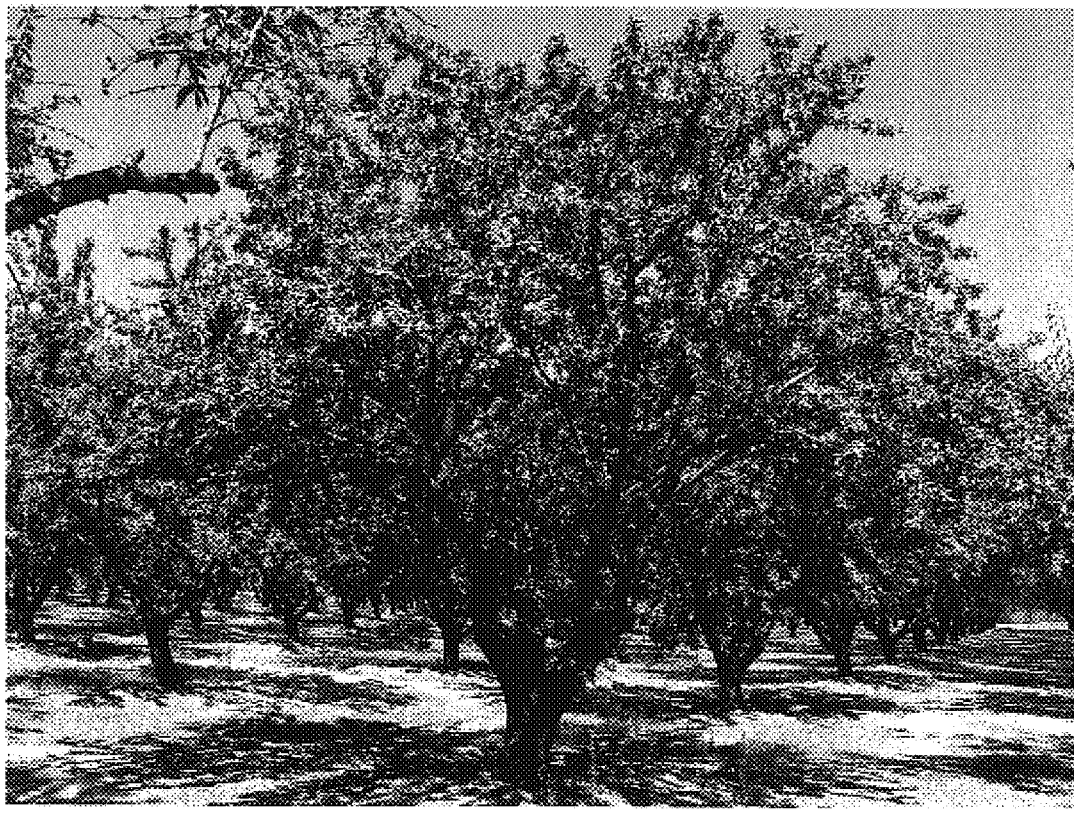
FIG. 1 is a picture of the 'Folsom' tree.
Figure 2:
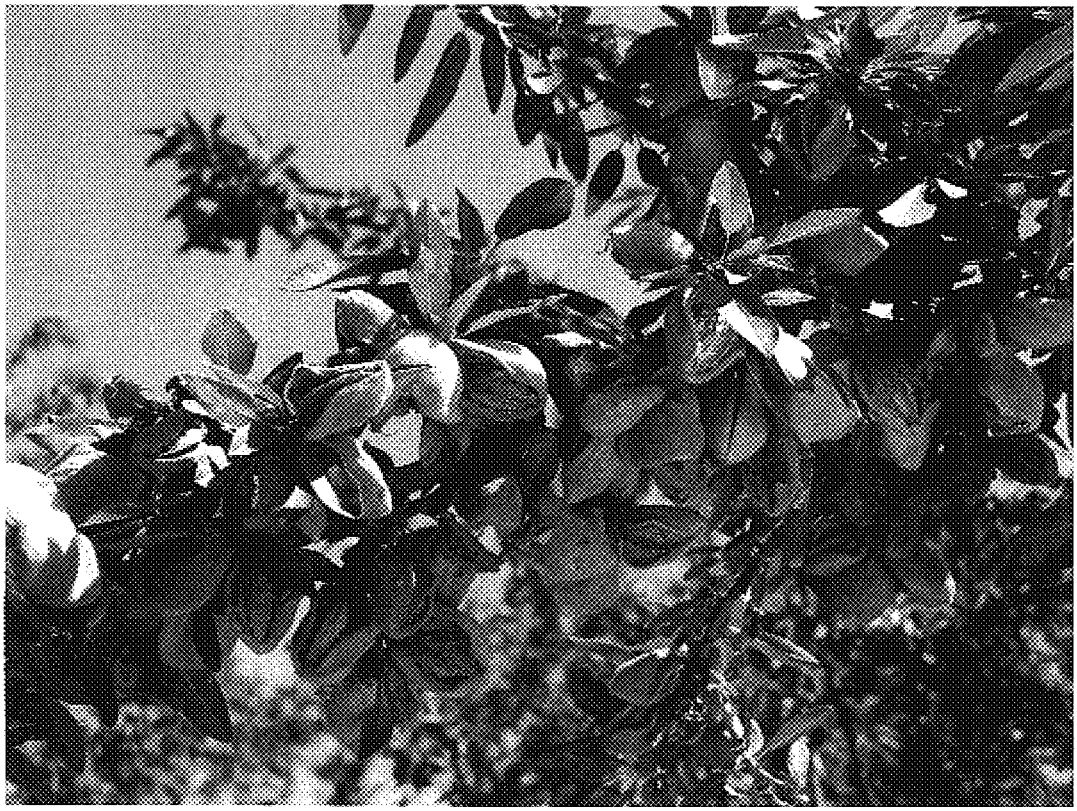
FIG. 2 is a picture of nuts and foliage.
Figure 3:
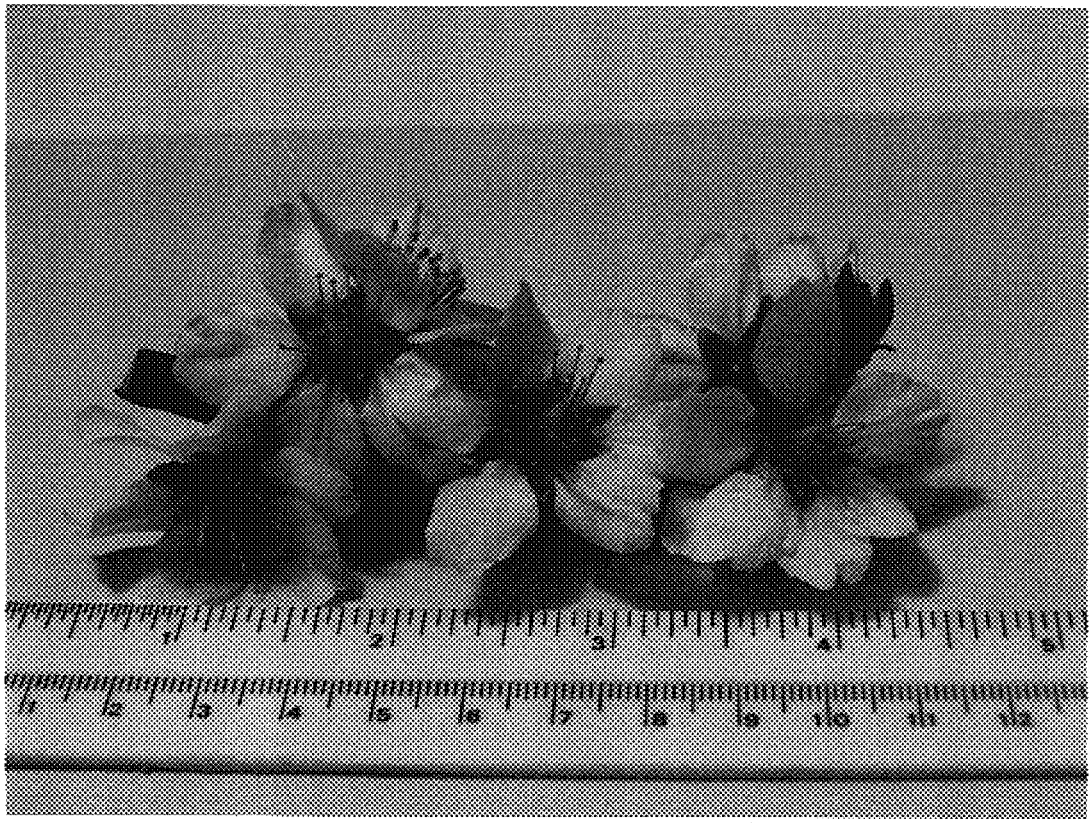
FIG. 3 is a picture of flower.
Figure 4:
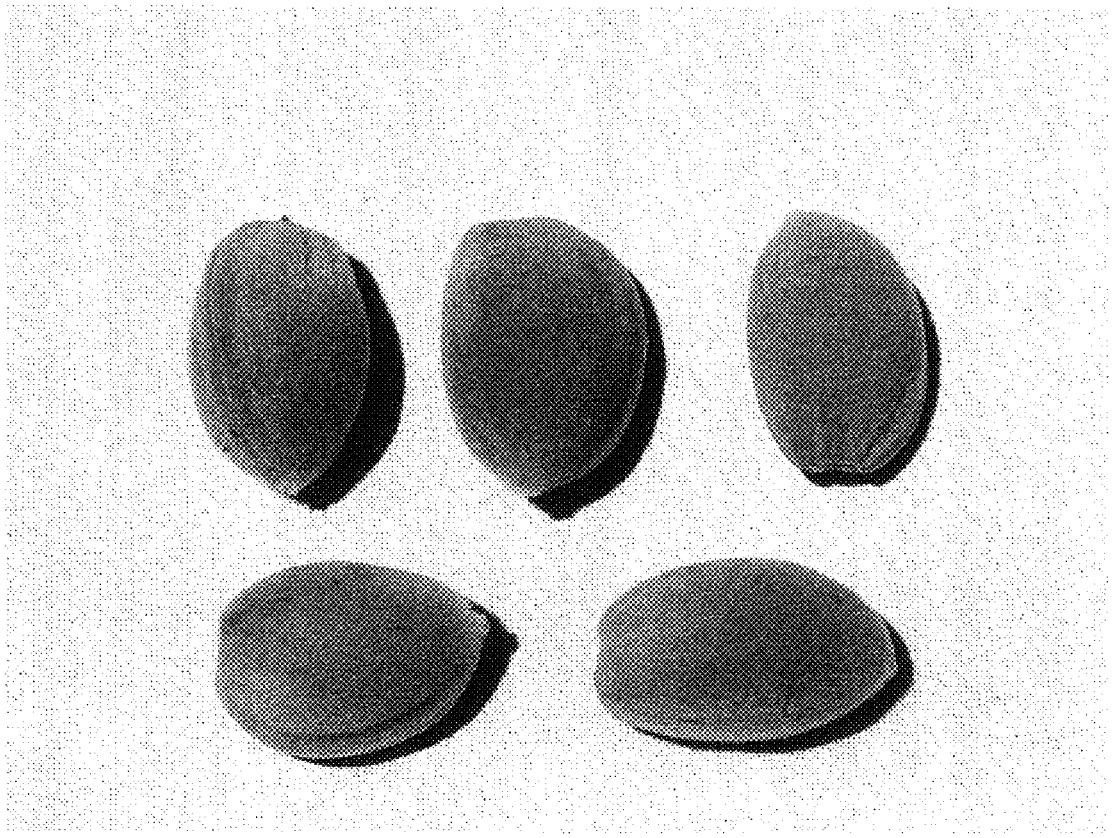
FIG. 4 is a picture of immature nuts.
Figure 5:
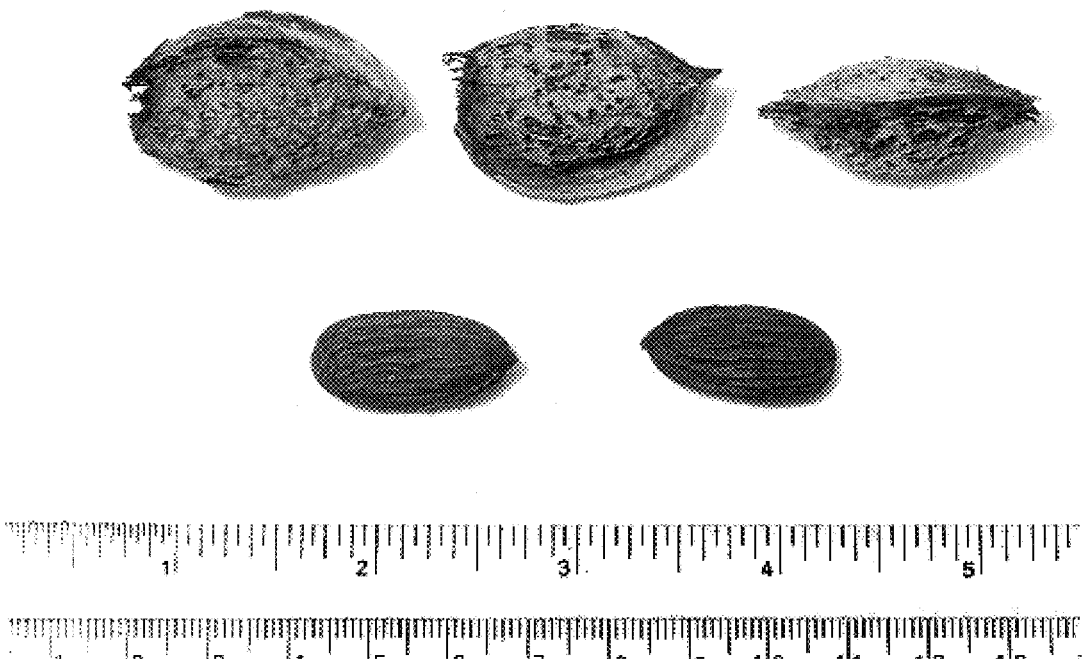
FIG. 5 is a picture of mature nuts.

The following detailed botanical description is based on observations of three year old trees, made during the 2004 growing season at Clovis, Calif. and Reedley Calif. All colors are described according to The Royal Horticultural Society Colour Chart, 3rd edition (1995). Botanical nomenclature is referenced by Harrington, H. D. and L. W. Durrell 1957, How to Identify Plants, The Swallow Press Incorporated. 203 pp. It should be understood that the characteristics described will vary somewhat depending upon fertilization, cultural practices, and climatic conditions, and can vary with location and season. Quantified measurements are expressed as an average of measurements taken from a number of individual plants of the new variety. The measurements of an individual plant, or any group of plants, of the new variety may vary from the stated average.

Tree:

*Size.*—Height 3.73 m, Width 3.77 m.

*Vigor.*—Medium; First year growth 1.5 to 2 meters, varies with soil and cultural methods.

*Density.*—Medium.

*Figure.*—Spreading. Primary limb angles approximately 40–45° dependent on pruning practices.

*Bearing.*—Regular.

*Production.*—Appears to be similiar to 'Nonpareil' almond.

*Chilling hours required.*—250–350 hours.

Trunk:

*Size.*—Diameter 11.1 cm at 40 cm above ground.

*Bark.*—Texture, rough; Color, Brown R.H.S. 200A with grey cast.

*Lenticels.*—Height 1.3 mm, width 4.6 mm, density 11 per $cm^2$, color brown R.H.S. 199B.

Branches:

*Size.*—Primary branch diameter 7.5 cm.

*Texture.*—Bark smooth on 1–4 year old wood. Rough on wood 5 years and older.

*Lenticels.*—Numerous, small to medium in size.

*Color.*—1 year old, brown R.H.S. 200D grey cast, sometimes interspersed with medium green R.H.S. 145A. 2 year old, grey green R.H.S. 197A to R.H.S. 197B.

Shoots:

*Size.*—Medium, variable from 6 to 65 cm in length.

*Form.*—Straight, generally lacking current year laterals.

*Texture.*—Smooth.

*Color.*—Medium green R.H.S. 145A. Generally lacking anthocyanin.

*Leaf buds.*—Terminal, short and pointed. Lateral, small and triangular. Length and width approximately 2 to 4 cm.

*Color.*—Dark brown, darker than R.H.S. 200A.

*Flower buds.*—Conical in shape, apex obtuse, buds 2 to 3 times larger than leaf buds.

*Color.*—Dark brown R.H.S. 200A to R.H.S. 200B.

*Position.*—Lateral, 0 to 4 flower buds per node.

*Nodes.*—5 to 35 in number. Internodal spacing approximately 1 to 2.5 cm.

Spurs:

*Position.*—Usually occur on older wood.

*Size.*—Thickness, 0. 3 to 0.9 cm. Length, 1 to 3.9 cm.

*Color.*—Brown, R.H.S. 200A with grey cast.

*Viability.*—May remain viable from 1 to 4 years producing both leaf and from 0 to 5 flower buds. Occasionally, short shoots may develop from a spur.

Leaves:

*Size.*—Medium, average length, 8.5 cm. Average width, 19 cm. Ratio of blade to length, approximately 0. 31.

*Shape.*—Long, elliptical, tapering to apex.

*Tip.*—Acuminate, tapering to a short, abrupt tip.

*Base.*—Rounded to slightly oblique.

*Thickness.*—Medium.

*Texture.*—Smooth.

*Margin.*—Crenate.

*Venation pattern.*—Reticulated.

*Blade color.*—Upper surface R.H.S. 146A. Lower surface R.H.S. 147B.

*Midrib.*—Distinct, upper surface color R.H.S. 146D. Lower surface color R.H.S. 145C.

*Leaf glands.*—Inconspicuous, globose, generally 0 to 6 present, alternate on petiole, occasionally occurring on leaf base.

*Petiole.*—Groove on upper surface. Diameter 1.1 mm. Ratio of petiole length to leaf length approximately 0.28.

*Color.*—Same as midrib.

*Stipules.*—Absent.

Inflorescence:

*Bloom.*—10% on Feb. 22, 2004 — Full on Feb. 27, 2004 at Reedley, Calif.

*Flower.*—Complete and perfect. Stamen and petal insertion, perigynous. Ovary, superior. Flower parts considered regular.

*Petals.*—Distinct, 5 to 6 present. Petals may overlap near their median margins when fully open.

*Petal shape.*—Broadly ovate, apex distinctly retuse. Base tapering to a short, abrupt claw.

*Petal length.*—1.5 to 2.0 cm.

*Petal width.*—1.3 to 1.4 cm.

*Color.*—Pink bud, apex is R.H.S. 65B. Full bloom, showy, pale white, lighter than R.H.S. 62D.

*Flower size.*—Medium, averaging 3.3 cm in diameter.

*Flower depth.*—3.4 mm.

*Sepals.*—5–6 present, length 0.8 to 1.2 cm.

*Sepal color.*—Varies from yellow-green R.H.S. 144B to greyed-purple R.H.S. 183C. A distinct midline R.H.S. 183C often present.

*Stamens.*—14 to 30 present. Length varies, but does not project beyond petals. Anthers versatile, filaments white, lacking pigment.

*Pistil.*—1, rarely 2 present. Length, 1 to 1.7 cm, generally straight and as long or longer than stamens. Pistil normally included in corolla, but may occasionally be exerted. Ovary and lower portion of style pubescent, upper portion of style and stigma lacking pubescence.

Immature fruit:

*Hull color.*—Grey Green R.H.S. 195A.

*Pubescence.*—Fine whitish grey evenly distributed over the hull surface.

*Form.*—Length to width, ovate, tapering to a blunt point at apex.

*Base.*—Straight.

*Apical view.*—Generally fusiform in shape.

*Ventral edge.*—Broadly rounded with a shallow but distinct suture line.

*Dorsal edge.*—Broadly curved from base to tip, being gently tapered at base and more rounded towards tip.

*Apical tip.*—Generally oblique to the first axis. Style rudiments often present.

*Hull texture.*—Short basal grooves present. Ventral suture line located on prominent ridge. A less distinct dorsal ridge is occasionally present. The remainder of the fruit surface is smooth and even.

*Peduncle attachment.*—Firmly attached to first, medium in size and round to oval in shape. Distinct depression observed when peduncle is separated from fruit.

Mature fruit:

*Dehiscence.*—Occurs along the ventral suture line. The nut separates easily from the hull frequently leaving the mesocarp attached to the hull.

*Nut size.*—Average length, 2.9 cm. Width 1.8 cm. Thickness, medium.
*Shape.*—Ovate.
*Apex.*—Acute, generally oblique to the axis.
*Shell.*—Soft, often split along ventral edge. Pores poorly developed, few in number.
*Base.*—Square to ventrally oblique.
*Peduncular scar.*—Small, inconspicous.
*Wing.*—Broad and thin.
*Color.*—Outer surface, R.H.S. 165C to R.H.S. 167D. Inner surface, R.H.S. 167D.
*Kernel size.*—Average length, 2.1 cm. Width, 1.2 cm. Thickness, medium.
*Shape.*—Ovate.
*Apex.*—Acute, oblique to the axis.
*Base.*—Generally truncate, rounded on ventral edge.
*Hilum.*—Ovate.
*Pellicle.*—Thin, color R.H.S. 164C. Percent of kernel to nut, approximately 63%. Number of doubles is low.
*Flavor.*—Sweet.
*Quality.*—Good.

Disease resistance: Appears to be similar to other almond cultivars grown under central valley growing conditions.

Insect resistance: Susceptibility likely similar to other soft-shell varieties, such as 'Nonpareil' grown in California.

I claim:

1. A new and distinct variety of almond tree as illustrated and described herein, which is characterized as to novelty by its ability to bloom and harvest in the early season.

* * * * *